(12) United States Patent
Jung et al.

(10) Patent No.: US 8,604,230 B2
(45) Date of Patent: Dec. 10, 2013

(54) POROUS CRYSTAL COMPRISING AMMONIA BORANE AND A PRODUCTION METHOD THEREFOR

(75) Inventors: Donghyun Jung, Daejeon (KR); Junho Kim, Seoul (KR); Minkyoung Kim, Seongnam-si (KR); Daejin Kim, Seoul (KR); Seunghoon Choi, Seongnam-si (KR); Kihang Choi, Seoul (KR); Jaheon Kim, Gwangju-si (KR); Kyungseok Jeong, Seoul (KR); Sangbeom Choi, Anyang-si (KR); Nakeun Ko, Incheon (KR)

(73) Assignee: Insilicotech Co., Ltd, Seongnam-si (KR)

( * ) Notice: Subject to any disclaimer, the term of this patent is extended or adjusted under 35 U.S.C. 154(b) by 262 days.

(21) Appl. No.: 13/259,829

(22) PCT Filed: Aug. 13, 2010

(86) PCT No.: PCT/KR2010/005370
§ 371 (c)(1),
(2), (4) Date: Sep. 23, 2011

(87) PCT Pub. No.: WO2011/019251
PCT Pub. Date: Feb. 17, 2011

(65) Prior Publication Data
US 2012/0016146 A1 Jan. 19, 2012

(30) Foreign Application Priority Data

Aug. 14, 2009 (KR) ........................ 10-2009-0075313

(51) Int. Cl.
*C07F 5/02* (2006.01)
(52) U.S. Cl.
USPC ...................................... 556/8; 564/9; 564/10
(58) Field of Classification Search
USPC ............................................. 556/8; 564/9, 10
See application file for complete search history.

(56) References Cited

U.S. PATENT DOCUMENTS

2008/0095684 A1  4/2008  Oshima et al.

OTHER PUBLICATIONS

Li, Yaoqi, et al., "Metal-Organic-Framework-Based Catalyst for Highly Efficient $H_2$ Generation from Aqueous $NH_3BH_3$ Solution", Chemistry—European Journal, 2009, pp. 8951-8954, vol. 15, Issue 36.
Xiong, Zhitao, et al., "High-capacity hydrogen storage in lithium and sodium amidoboranes", Nature Materials, Feb. 2007, pp. 138-141, vol. 7.
Xiong, Zhitao, et al., "Interaction of lithium hydride and ammonia borane in THF", Chemical Communications, 2008, pp. 5595-5597.
Stephens, Frances H., et al., "Ammonia-borane: the hydrogen source *par excellence*?", Dalton Trans., 2007, pp. 2613-2626.
International Searching Authority, International Search Report of PCT/KR2010/005370, dated Apr. 27, 2011.

*Primary Examiner* — Porfirio Nazario Gonzalez
(74) *Attorney, Agent, or Firm* — Sughrue Mion, PLLC

(57) ABSTRACT

Disclosed does a porous crystal comprising ammonia borane in which the ammonia borane is chemically bonded thereto by a chemical reaction while a porous crystal structure is maintained.

15 Claims, 2 Drawing Sheets

POROUS CRYSTAL COMPRISING AMMONIA BORANE AND A PRODUCTION METHOD THEREFOR

TECHNICAL FIELD

The present invention relates to a porous crystal in which ammonia borane capable of storing a hydrogen gas is bonded to a frame and a method for producing the same.

BACKGROUND ART

Recently, many countries throughout the world have tried to develop wind power, tidal power, geothermal power, solar power, and hydrogen gas, etc. as an energy source for replacing depletive fossil fuel. Among them, hydrogen gas has the highest energy efficiency per unit mass and no harmful byproducts during combustion, and thus, research on the preparation, storage, and transportation, etc. thereof has been conducted. In particular, in accordance with the practical use of a fuel cell, a material capable of efficiently storing the hydrogen gas has been developed.

Currently, materials capable of storing the hydrogen gas include metal hydride, ammonia borane ($NH_3BH_3$), carbon nanotube, carbon compounds such as active carbon, zeolite, a metal-organic framework (MOF), a covalent organic framework (COF), and the like. Among them, when it is assumed that ammonia borane uses all 3 equivalent of hydrogen, ammonia borane can store 19.6 wt % of hydrogen, such that a high hydrogen storage amount is exhibited. Accordingly, a method for storing and transporting hydrogen by using ammonia borane has been actively studied. However, the largest problem of practical use of ammonia borane is to regenerate the used ammonia borane. If hydrogen is removed from ammonia borane, a high molecular weight material with very large viscosity such as polyborazylene as well as a volatile material such as borazine is generated, and thus, it is very difficult to regenerate ammonia borane by adding hydrogen again. This regeneration problem is one of the largest reasons for classifying ammonia borane as only an offboard hydrogen storage material, not an onboard hydrogen storage material.

The metal-organic frameworks (MOFs) capable of storing hydrogen by a physical adsorption among other hydrogen storage materials are a kind of organic-inorganic hybrid compound, and are a material in which metal and an organic ligand are three-dimensionally linked to each other, and the organic ligand is used as a linker. Specifically, as shown in FIG. 1, the MOFs means a material in which the organic ligand is coordinated to two or more metals, and each of the coordinated metals is serially coordinated to one or more other organic ligands, thereby forming many tiny spaces, i.e. a network structure with pores, inside the framework.

This metal-organic framework is manufactured by various producing methods. For example, the MOFs can be prepared through a substitution reaction of an organic ligand ion by using metal salt as a metal source. In detail, in such preparation, zinc nitrate [$Zn(NO_3)_2$] as a metal source, and a dicarboxylic acid compound as a ligand are mainly used so as to prepare the framework (O. M. Yaghi et al. Science, 2003, vol. 300, p. 1127; WO 02/088148).

In addition, there is a method for preparing an isoreticular metal-organic framework (IRMOF) by using zinc as a metal source to thereby form zinc oxides ($Zn_4O$) as a core and by using an organic ligand such as a dicarboxylic group. Further, there is a method for preparing a metal-organic framework by using, instead of zinc, the metal ion such as Cu and Fe as a core, and using tridentate or multidentate organic ligands.

As another porous crystal structure, many efforts for forming a covalently bonded network structure composed of only organic materials have been made, and recently, a group of professor, Yaghi at the University of California, Berkeley synthesized a covalent organic framework including a cluster of boron and presented the contents thereof [US2006/0154807 A1]. According to the contents of the patent, it is possible to constitute a network formed of a covalent bond by bonding each bonding group with at least two clusters of boron.

In the real synthesis, a two-dimensional plane network is generated by a polycondensation reaction of a benzene diboronic acid (BDBA), lamination is formed through an interaction between the generated plane networks, and thus, the covalent organic framework has crystallinity. In this case, a length of an entrance of the generated pore is about 15 Å.

However, the storage capacity of the physical adsorption hydrogen storage material is largely insufficient in order to be commercialized, and particularly, since the storage capacity of the material at room temperature does not approach 1 wt % even under high pressure, and thus, a groundbreaking idea is required for largely increasing capacity.

In a prior art, there was an effort for changing a hydrogen storage property of ammonia borane by including ammonia borane in a porous material such as zeolite, but since ammonia borane is physically included in the pore of the porous material and the property of the crystal structure is not substantially changed, there is a performance improvement in that a speed of a dehydrogenation reaction is increased, but a regeneration problem of ammonia borane is still not solved.

DISCLOSURE

Technical Problem

The present inventors found that since various products generated after ammonia borane generates hydrogen include a polymer material having a high molecular weight as well as a volatile material having a low molecular weight, it is very difficult to perform a next regeneration process, such that there is a large problem in commercializing ammonia borane. In addition, the present inventors found that since the porous material that includes the metal-organic framework or the covalent organic framework can store hydrogen by only the physical adsorption, there is a problem in that the storage capacity of the porous material is remarkably decreased at room temperature.

Accordingly, the present invention has been made in an effort to provide a hydrogen storage material having a double mode, which can directly use hydrogen chemically included in ammonia borane by chemically directly bonding ammonia borane or a derivative thereof to with a porous crystal structure including a metal-organic framework or a covalent organic framework and simultaneously use hydrogen storage capability which a porous material can have by physical adsorption, and a method for preparing the same.

Technical Solution

According to an aspect of the present invention, there is provided a porous crystal comprising ammonia borane in which the ammonia borane is chemically bonded thereto by a chemical reaction while a porous crystal structure is maintained.

In accordance with another aspect of the present invention, there is provided a porous crystal comprising ammonia borane, in which the porous crystal structure is a metal-organic framework or a covalent organic framework.

Advantageous Effects

In a porous crystal comprising ammonia borane according to the present invention, the ammonia borane or a derivative thereof is chemically bonded to a frame of a porous crystal itself, thereby allowing hydrogen storage capability of the ammonia borane as it is to be used even room temperature. In addition, since the ammonia borane is strongly bonded to the frame, it is possible to prevent products generated by a dehydrogenation reaction from being polymerized after the products meet each other to cause a reaction, thereby simplifying a regeneration process and using a physical adsorption capability which a porous crystal structure may have as it is.

BEST MODE

Hereinafter, the present invention will be described in detail.

The present invention is characterized in that ammonia borane is chemically bonded to a porous crystal structure.

In general, ammonia borane is dehydrogenated at a high temperature of 200° or higher, and thus, various products are generated, and herein, a polymer having high viscosity as well as a volatile material having a low molecular weight is formed. Since there is no simple method for reducing the products into ammonia borane again by regenerating the formed products as described above, there is a large problem in commercializing.

Since the physical adsorption that is a method for storing hydrogen in a porous material adsorbs an adsorption material on an adsorbent by only van der Waals force without change of a molecular structure or electron transfer between the adsorption material and the adsorbent unlike a chemical adsorption, a sufficient amount of hydrogen is not stored at room temperature. Therefore, when the hydrogen gas is stored by using a conventional coordination polymer crystal, and kept or transported, an expensive apparatus for constantly maintaining high pressure is needed.

Therefore, in the present invention, ammonia borane or a derivative thereof is directly bonded into a porous crystal, it is possible to basically prevent generation of products having high molecular weight caused by the reaction between the generated products even though ammonia borane is dehydrogenated, and thus, ammonia borane can be easily regenerated, and also since ammonia borane each independently exists, utilization of hydrogen may be increased.

Figure 1:
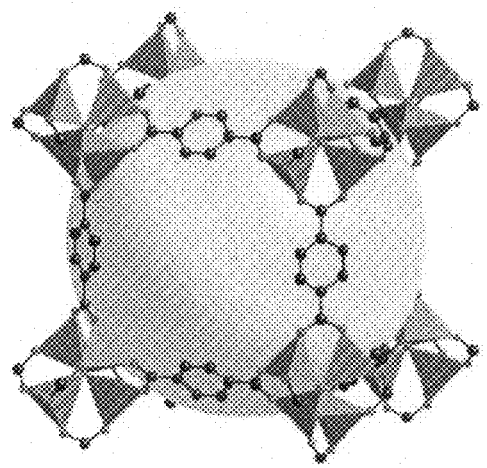
FIG. 1 is a three-dimensional structure view that illustrates a unit lattice of MOF-5 [$Zn_4(O)(C_8H_4O_4)_3$] in a conventional coordination polymer porous crystal having a metal-organic framework.
Figure 2:
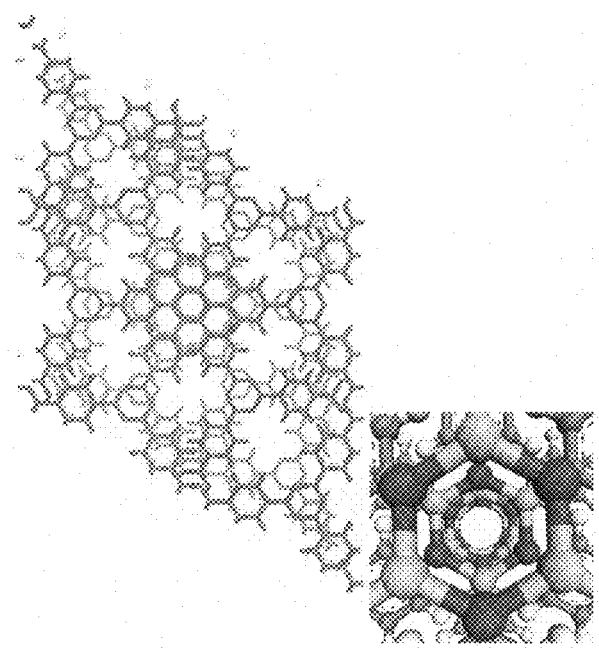
FIG. 2 is a structure view that illustrates an overlapping structure of a planar structure of COF-1 [$(C_3H_2BO)_6(C_9H_{12})$] in a conventional porous crystal having a covalent organic framework.
Figure 3:
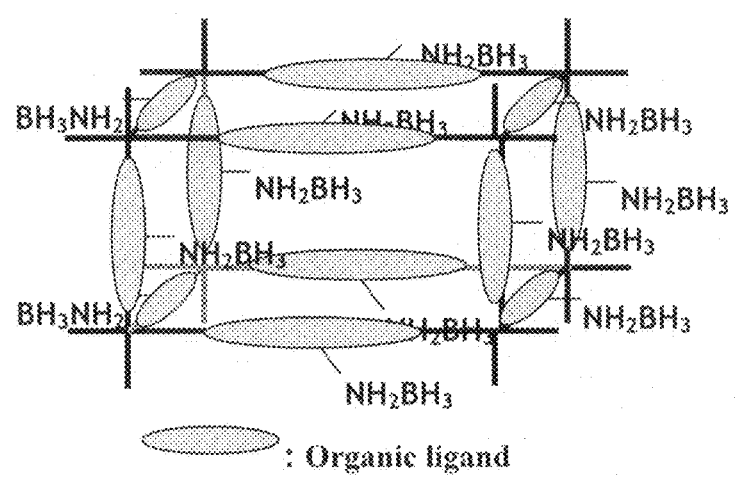
FIG. 3 is a mimetic diagram of a porous crystal to which ammonia borane is bonded, which is generated according to the present invention.

In the present invention, the porous crystal structure, as shown in FIG. 1, is a metal-organic framework in which two or three dimensional porous structures are formed by coordinate bonding metal to the organic ligand. The metal-organic framework includes an organic ligand and a metal ion, and has a porous framework in which the organic ligand is chemically bonded to two or more metal ions, and the chemically bonded metal ions are serially chemically bonded to one or more other organic ligands.

In detail, the metal-organic framework used in the present invention comprises an organic ligand containing a functional group that can be additionally chemically reacted with other material. For example, since the organic ligand has a functional group such as a hydrazine group (—$NHNH_2$) or an amine group (—$NH_2$), the functional group is directly reacted with $BH_3$ or the amine group, which is generated after a functional group such as aziridine ($CH_2H_5N$) that can form primary amine by reaction with the amine group (—$NH_2$), is reacted with $BH_3$, and then, the porous crystal in which ammonia borane is bonded to thereto is finally formed.

The metal-organic framework according to the present invention may be represented by the following Formula 1, but is not limited thereto.

$$[(M_aO_b)(L_1)_c(L_2)_d]_z \quad \text{[Formula 1]}$$

In Formula 1,

M is one or more metals selected from the group consisting of metal belonging to Groups 3 to 16, lanthanium metal, and actinium metal, $L_1$ and $L_2$ are each independently

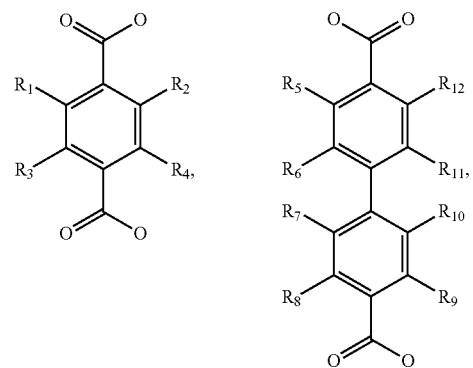

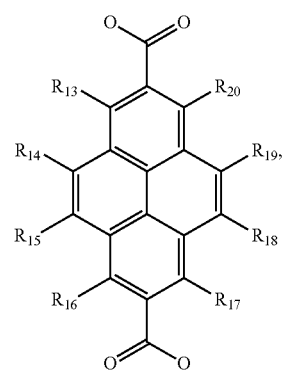

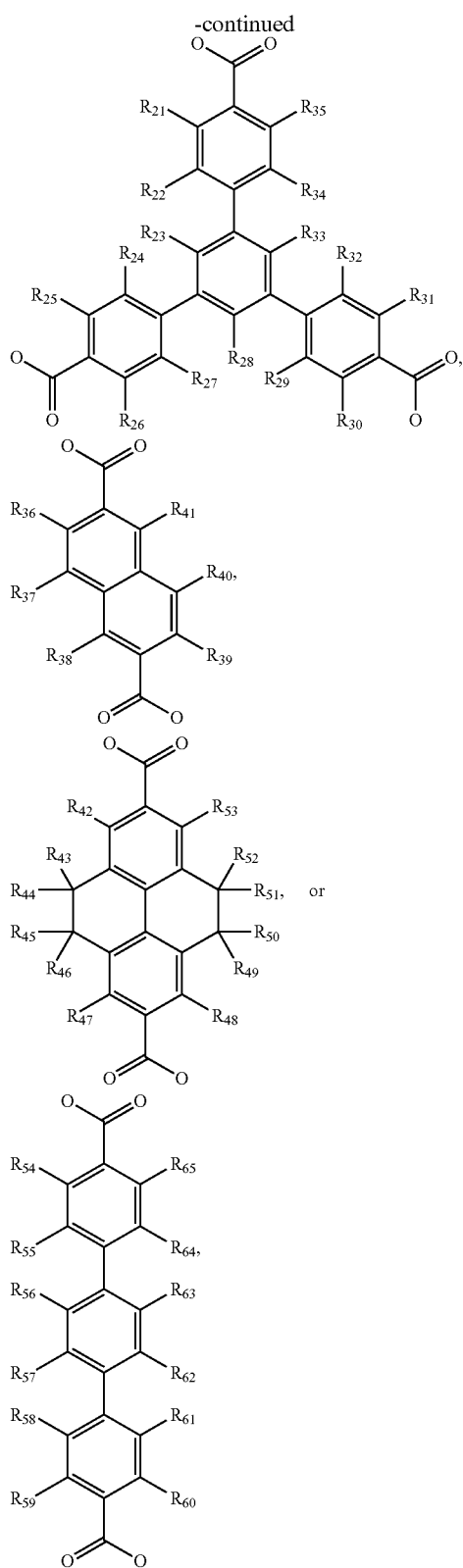

$R_1$ to $R_{65}$ are independently H; $NH_2$; $NHNH_2$; OH; COOH; CHO; CN; Cl; Br; I; NCO; OCN; $NCSNH_2$; alkyl that is substituted or unsubstituted by $NH_2$, $NHNH_2$, OH, COOH, CHO, CN, Cl, Br, I, $(C=O)_2O$, $(C=O)_2NH$, NCO, OCN or NCS; alkoxy; a functional group including sulfur; a functional group including Si; nitro group; a functional group including boron; a functional group including phosphorus or an ester group, adjacent two of $R_1$ to $R_{65}$ groups may form a $(C=O)_2O$ (carboxylic acid anhydride) group or a $(C=O)_2NH$ (imide) group, in each L1 and L2, at least one of $R_1$ to $R_{65}$ is $NH_2$, OH, COOH, CHO, CN, Cl, Br, I, $(C=O)_2O$, $(C=O)_2NH$, NCO, OCN, NCS, or alkyl substituted with OH, COOH, CHO, CN, Cl, Br, I, NCO, OCN or NCS, z is an integer of 1 to ∞, a is 0<a≤100, b is 0≤b≤100, c is 0≤c≤300, d is 0≤d≤300, and at least one of c and d is not 0.

z may be $8 \leq z \leq 10^{23}$.

Examples of the metal-organic framework according to the present invention may be represented by the following Formula 2 or Formula 3, but the examples are not limited thereto.

[Formula 2]

$[Zn_4O]_n[L]_{3n}$,

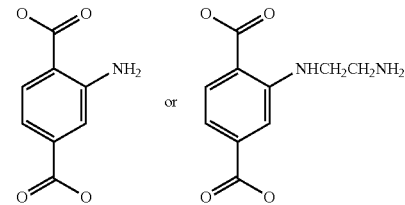

[Formula 3]

$[Zn_4O]_{3n}[(L_1)_3(L_2)_4]_n$,

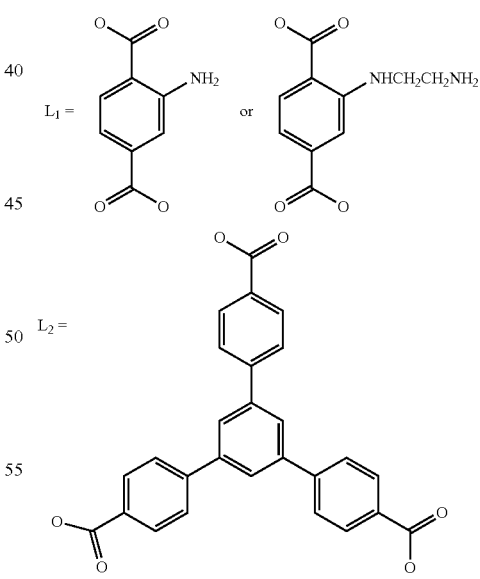

In Formulas 2 and 3, n is an integer of 1 to ∞.

Examples of the porous crystal having the final organic-metal framework in which borane is bonded to —$NH_2$ group of Formulas 2 and 3 through an additional chemical reaction include, but are not limited to, porous crystals presented by the following Formula 4 to Formula 7.

[Formula 4]

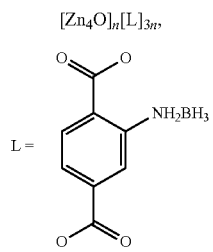

[Formula 5]

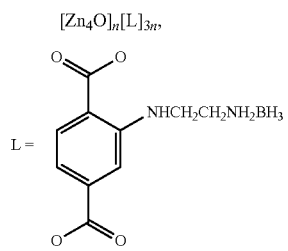

[Formula 6]

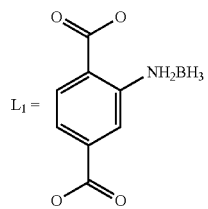

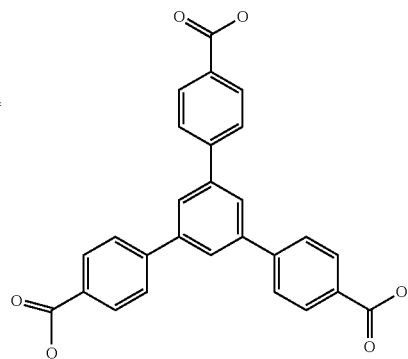

[Formula 7]

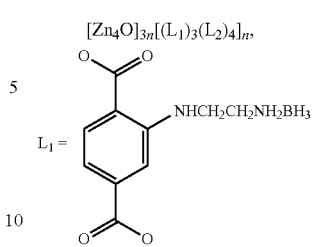

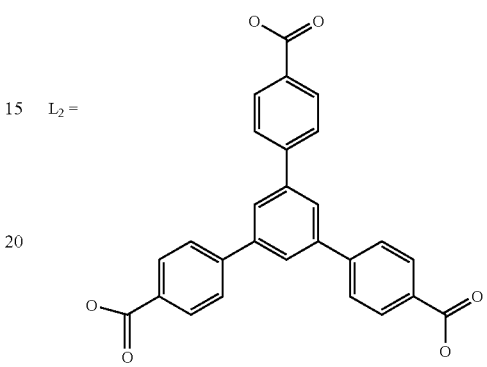

In the above Formulas, n is an integer of 1 to ∞.

The porous crystal having the covalent organic framework means a compound of a crystal structure having pores by two or three dimensionally bonding between organic compounds having functional groups that can perform a polycondensation reaction. Since this porous crystal maintains a stable porous structure even though a solvent or a guest molecule is adsorbed or desorbed in the pore, the porous crystal is useful in storing gas such as hydrogen gas.

Such covalent organic framework may comprise a linear or cyclic boron-containing cluster represented by Formula 8 or Formula 9.

[Formula 8]

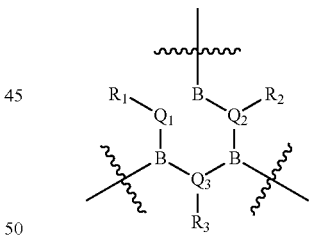

[Formula 9]

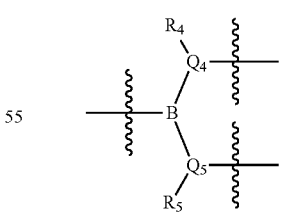

In Formulas 8 and 9, $Q_1$ to $Q_5$ are each independently an element belonging to Group 15 or 16 of a periodic table, with proviso that when Q1 to Q2 are each independently an element of Group 15, $R_1$ to $R_5$ are each independently hydrogen, a $C_1$-$C_{12}$ alkyl group, a $C_6$-$C_{12}$ aryl group, or halogen, and when $Q_1$ to $Q_5$ are each independently an element of Group 16, $R_1$ to $R_5$ do not exist.

Examples of the linear or cyclic boron-containing cluster include

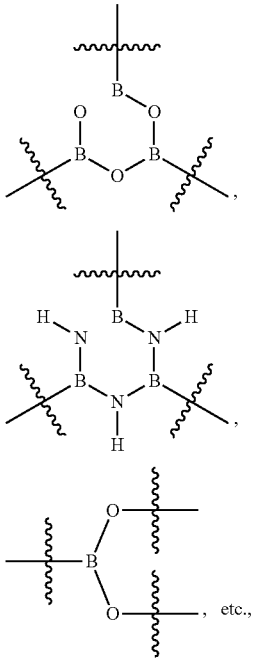

but the present invention is not limited to.

The linear or cyclic boron-containing cluster according to the present invention is covalently bound to the same or different two or three $C_6$-$C_{204}$ aromatic ring groups to form a building block.

The $C_6$-$C_{204}$ aromatic ring group may be represented by any one Formula of the following Formula 10, Formula 11, Formula 12, Formula 13, and Formula 14, but are not limited thereto.

[Formula 10]

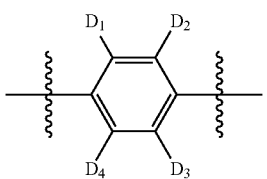

[Formula 11]

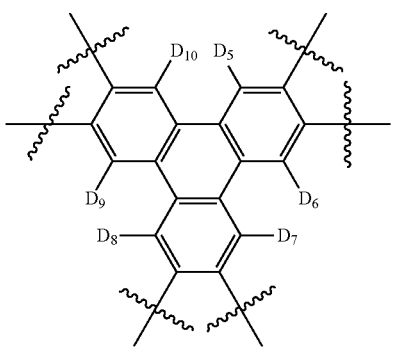

[Formula 12]

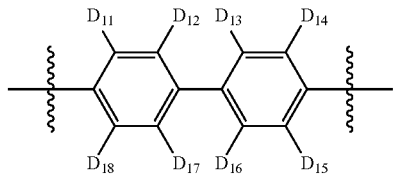

[Formula 13]

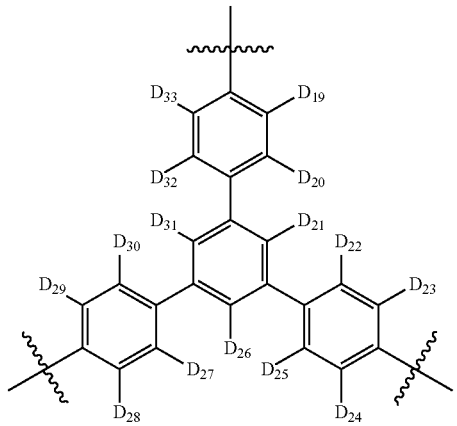

[Formula 14]

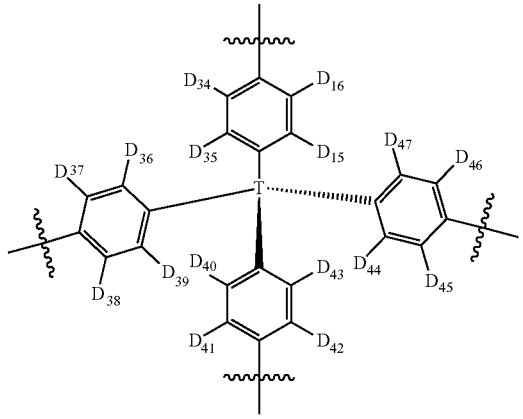

In the above Formulas, $D_1$ to $D_{47}$ are each independently a group selected from the group consisting of hydrogen; a $C_1$-$C_{12}$ alkyl group; a $C_1$-$C_{12}$ alkyl group substituted with one or more substituent groups selected from the group consisting of $NH_2$, $NHNH_2$, OH, COOH, CHO, CN, Cl, Br, I, $(C=O)_2O$, $(C=O)_2NH$, NCO, OCN, and NCS; a $C_6$-$C_{12}$ aryl group; a $C_1$-$C_{12}$ alkoxy group; $NH_2$; $NHNH_2$; OH; COOH; CHO; CN; Cl; Br; I; $(C=O)_2O$; $(C=O)_2NH$; NCO; OCN; NCS; a functional group including sulfur; a functional group including Si; nitro group; a functional group including boron; a functional group including phosphorus; and an ester group, T is an element that can form a regular tetrahedron structure, and in each aromatic cycle group, at least one of $D_1$ to $D_{47}$ should be $NH_2$; OH; COOH; CHO; CN; Cl; Br; I; $(C=O)_2O$; $(C=O)_2NH$; NCO; OCN; NCS; or a $C_1$-$C_{12}$ alkyl group substituted with one or more substituent groups selected from the group consisting of $NH_2$, OH, COOH, CHO, CN, Cl, Br, I, $(C=O)_2O$, $(C=O)_2NH$, NCO, OCN, and NCS.

Non-limiting examples of the $C_6$-$C_{204}$ aromatic cyclic group include, but are not limited to,

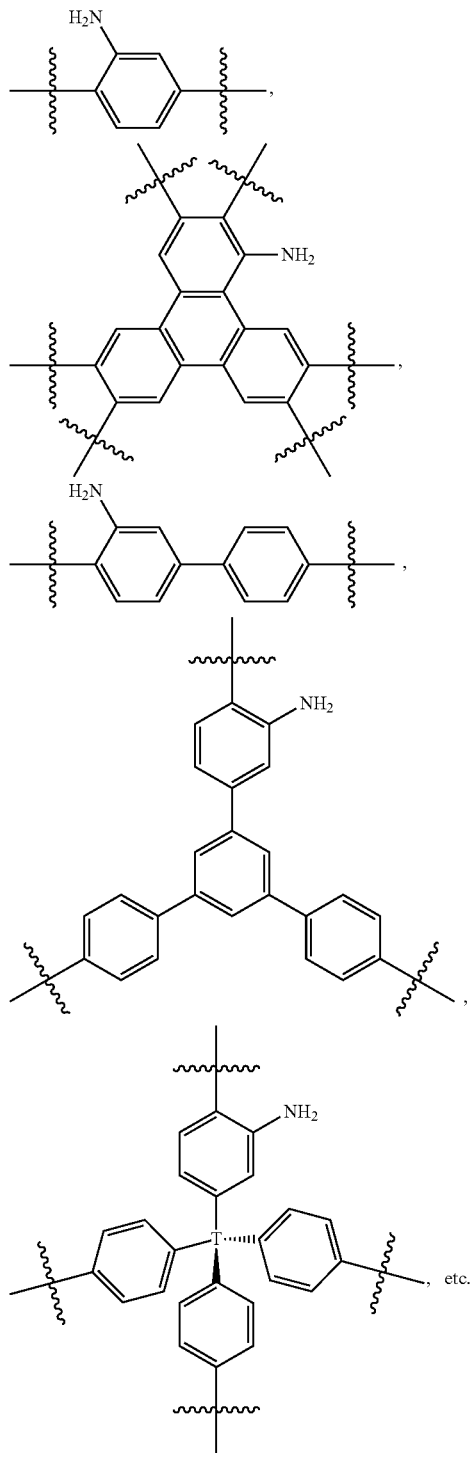

etc.

The above linear or cyclic boron-containing cluster is covalently bound to the same or different two or three $C_6$-$C_{204}$ aromatic cyclic groups, and thus, the building block having various shapes may be formed.

When one cyclic boron-containing cluster represented by Formula 8 is covalently bonded to three $C_6$-$C_{204}$ aromatic ring groups represented by Formula 10, a building block represented by the following Formula 15 may be formed.

[Formula 15]

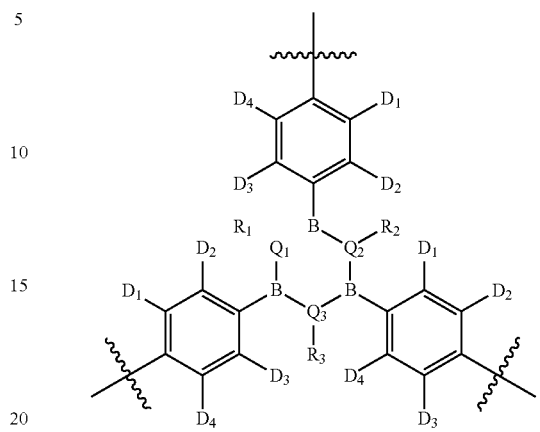

In Formula 15, $Q_1$ to $Q_3$ and $R_1$ to $R_3$ are the same as those defined by Formula 1, and $D_1$ to $D_4$ are the same as defined in Formula 10.

Examples of the building block represented by Formula 15 include a building block represented by the following Formula 15a and a building block represented by the following Formula 15b, but the present invention is not limited thereto.

[Formula 15a]

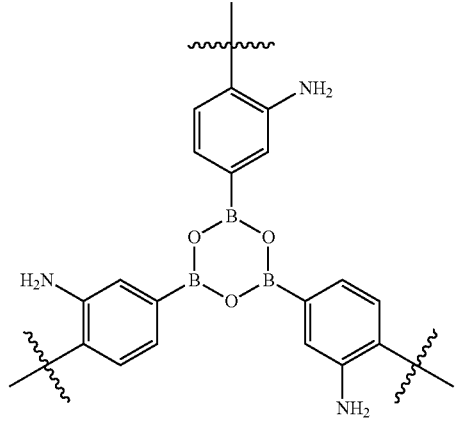

[Formula 15b]

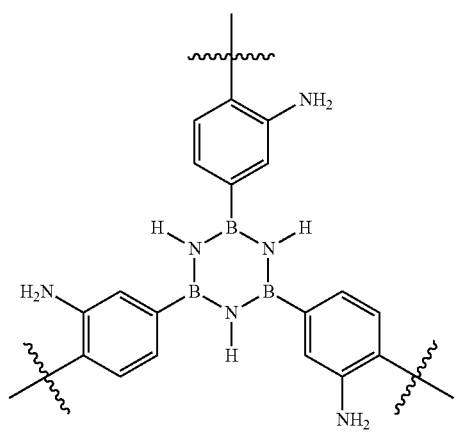

When three linear boron-containing clusters represented by Formula 9 are covalently bonded to three $C_6$-$C_{204}$ aromatic ring groups represented by Formula 10 and one $C_6$-$C_{204}$ aromatic ring group represented by Formula 11, a building block represented by the following Formula 16 may be formed.

[Formula 16]

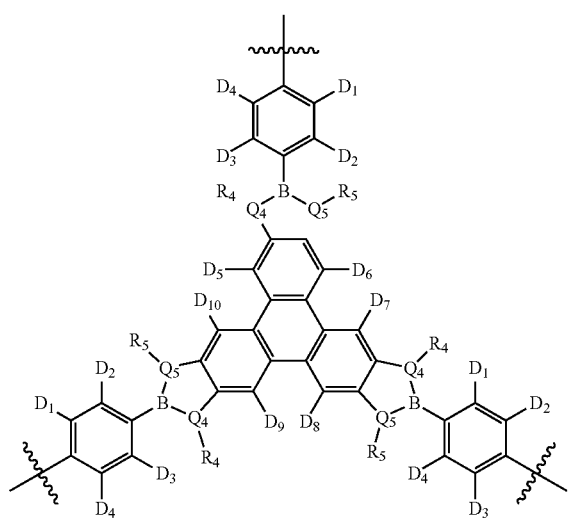

In Formula 16, $Q_4$ to $Q_5$ and $R_4$ to $R_5$ are the same as defined in Formula 9, and $D_1$ to $D_{10}$ are the same as defined in Formula 10 and Formula 11.

Examples of the building block represented by Formula 16 include, but are not limited to, a building block represented by the following Formula 16a.

[Formula 16a]

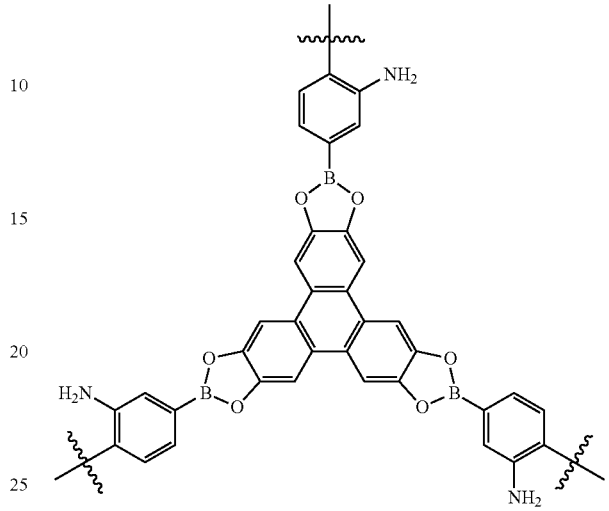

In the planar layer of the organic framework according to the present invention, the $C_6$-$C_{204}$ aromatic ring group constituting the building block (first building block) represented by Formula 15 or Formula 16 may be covalently bonded not only to the linear or cyclic boron-containing cluster constituting the first building block, but also to the linear or cyclic boron-containing cluster constituting another adjacent building block (second building block) having the same structure as the first building block, and also the linear boron-containing cluster of the second building block may be covalently bonded to the $C_6$-$C_{204}$ aromatic ring group of yet another adjacent building block (third building block) having the same structure as the first building block, in a chain-like manner. The formed planar layer formed as described-above may have various structures.

When the planar layer of the present invention is formed by serial bonding of the building blocks represented by Formula 15, the planar layer may be represented by the following Formula 17.

[Formula 17]

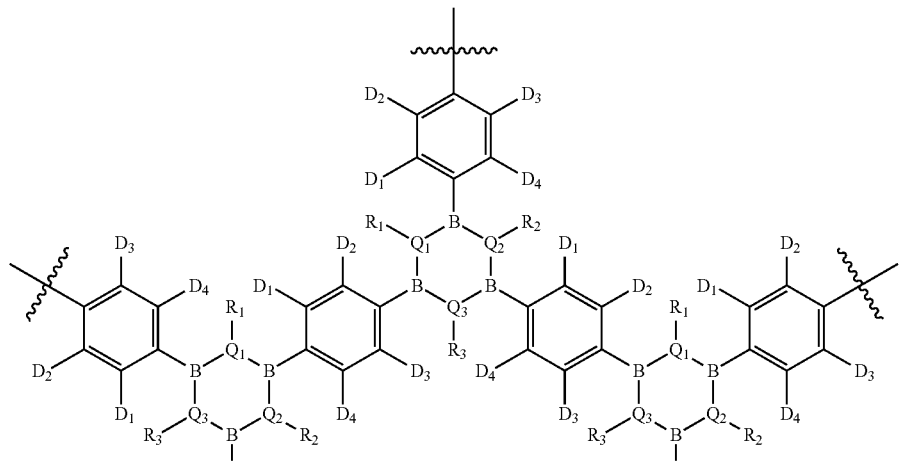

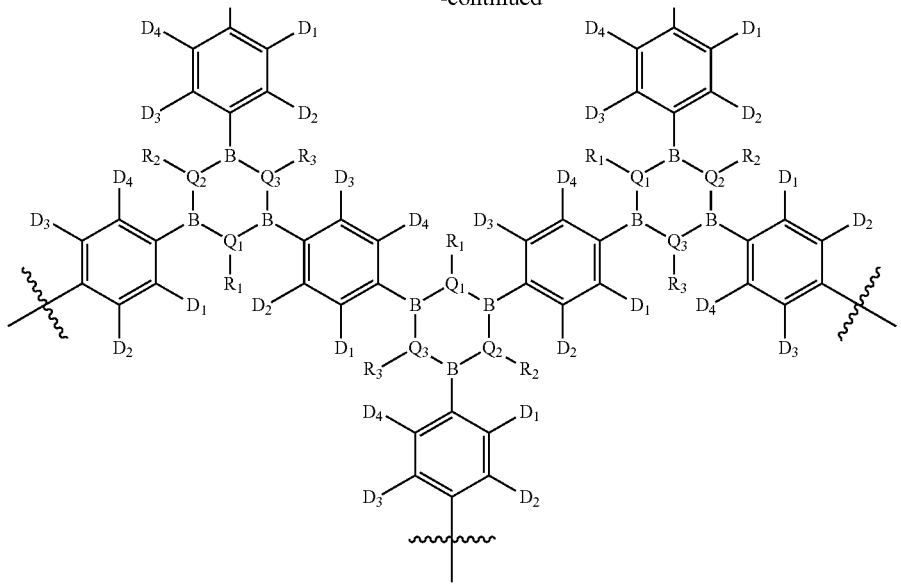
In Formula 17, $Q_1$ to $Q_3$ and $R_1$ to $R_3$ are the same as defined in Formula 8, and $D_1$ to $D_4$ are the same as defined in Formula 10.
Examples of the planar layer represented by Formula 17 include, but are not limited to, a planar layer represented by Formula 17a and a planar layer represented by Formula 17b.
[Formula 17a]
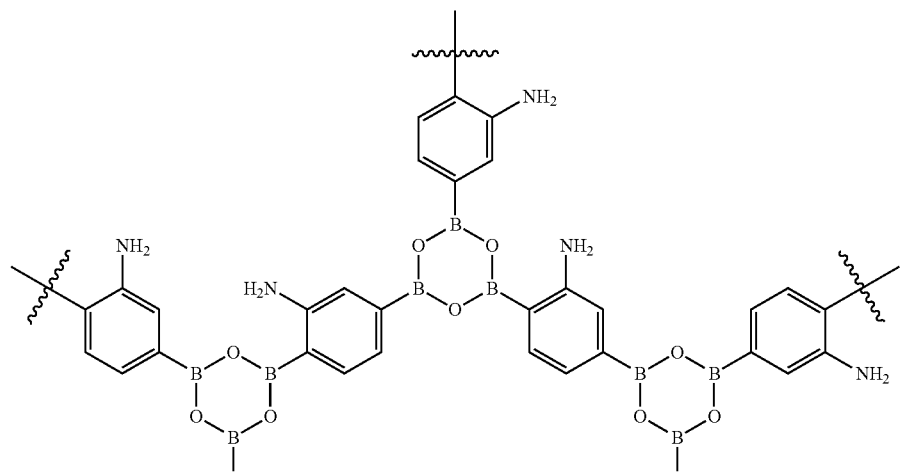

-continued
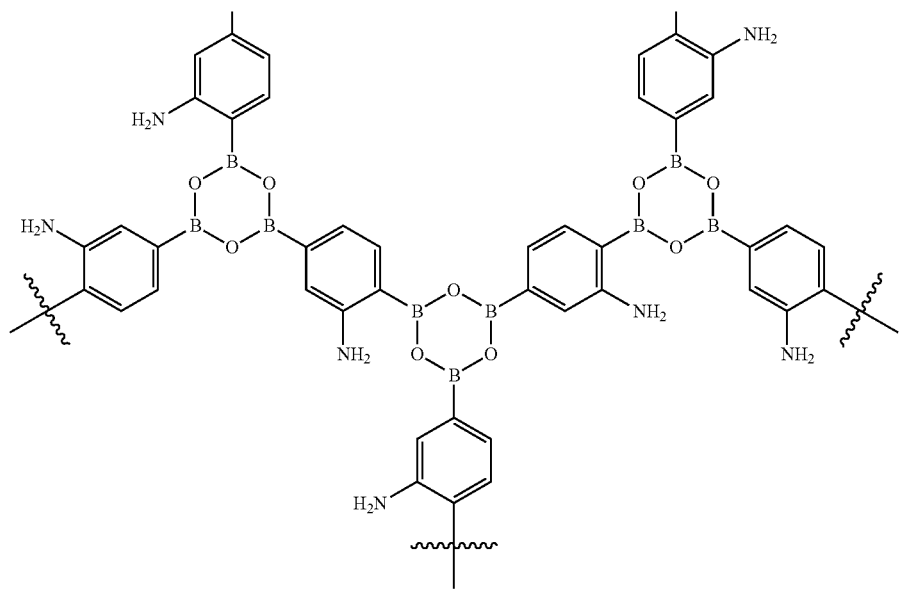
[Formula 17b]
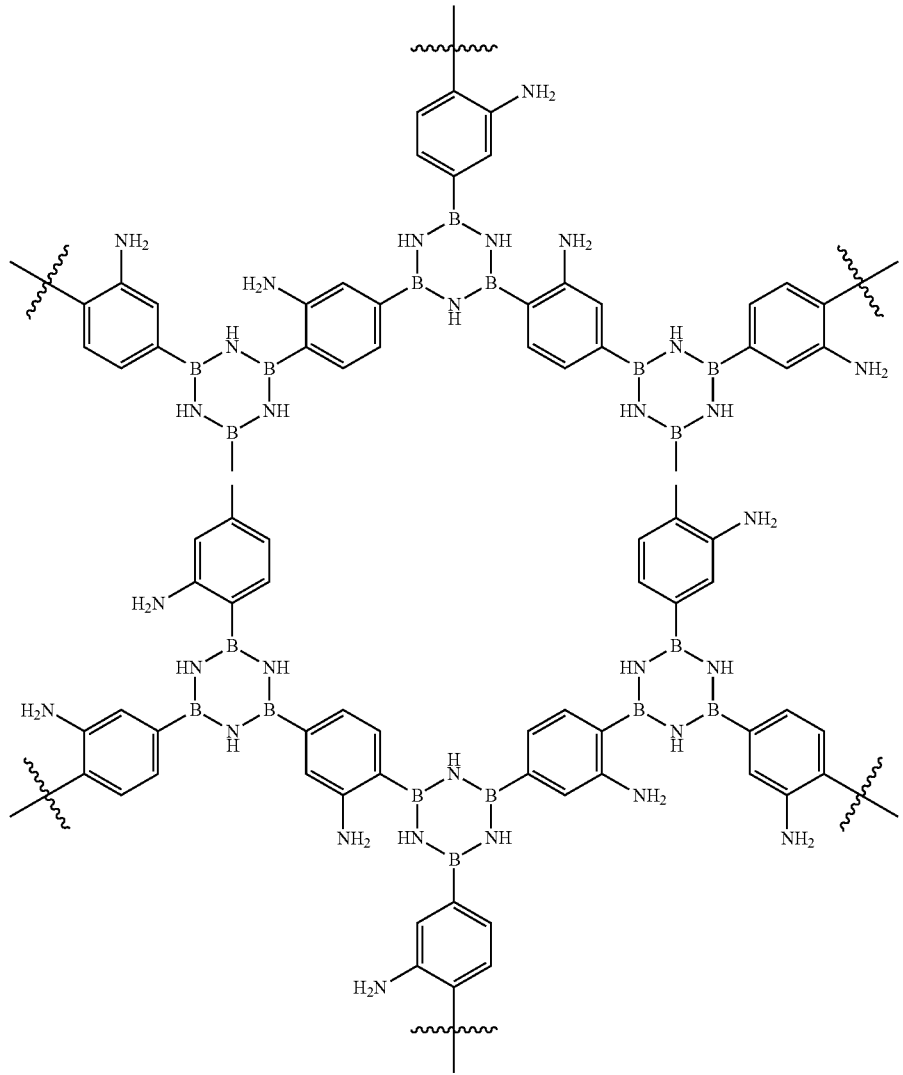

When the planar layer of the present invention is formed by serial bonding of the building block represented by Formula 15, the planar layer may be represented by the following Formula 18:
[Formula 18]
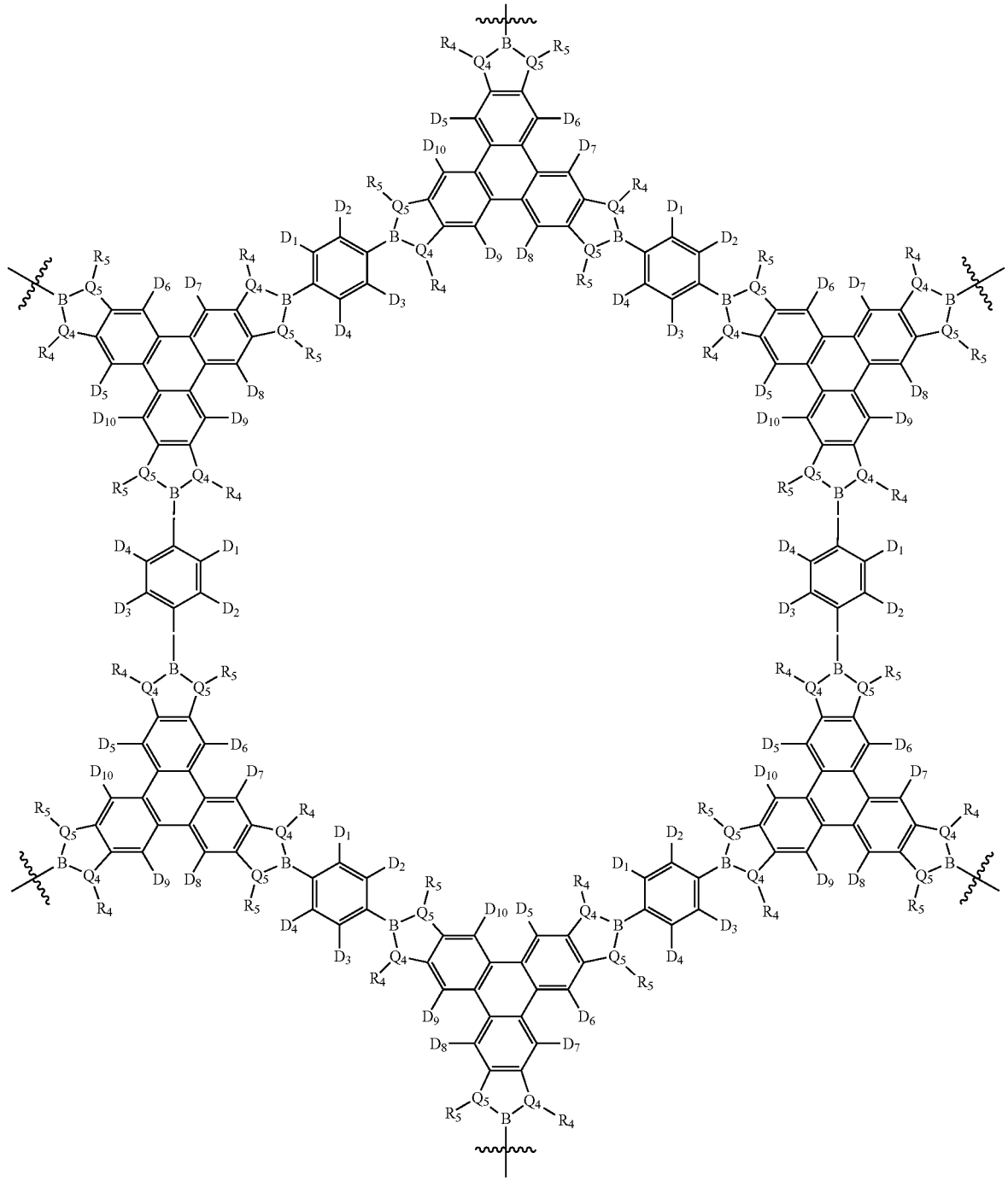

In Formula 18, $Q_4$ to $Q_5$ and $R_4$ to $R_5$ are the same as defined in Formula 9, and $D_1$ to $D_4$ are the same as defined in Formula 10.
Examples of the planar layer represented by Formula 18 include, but are not limited to, a planar layer represented by Formula 18a.
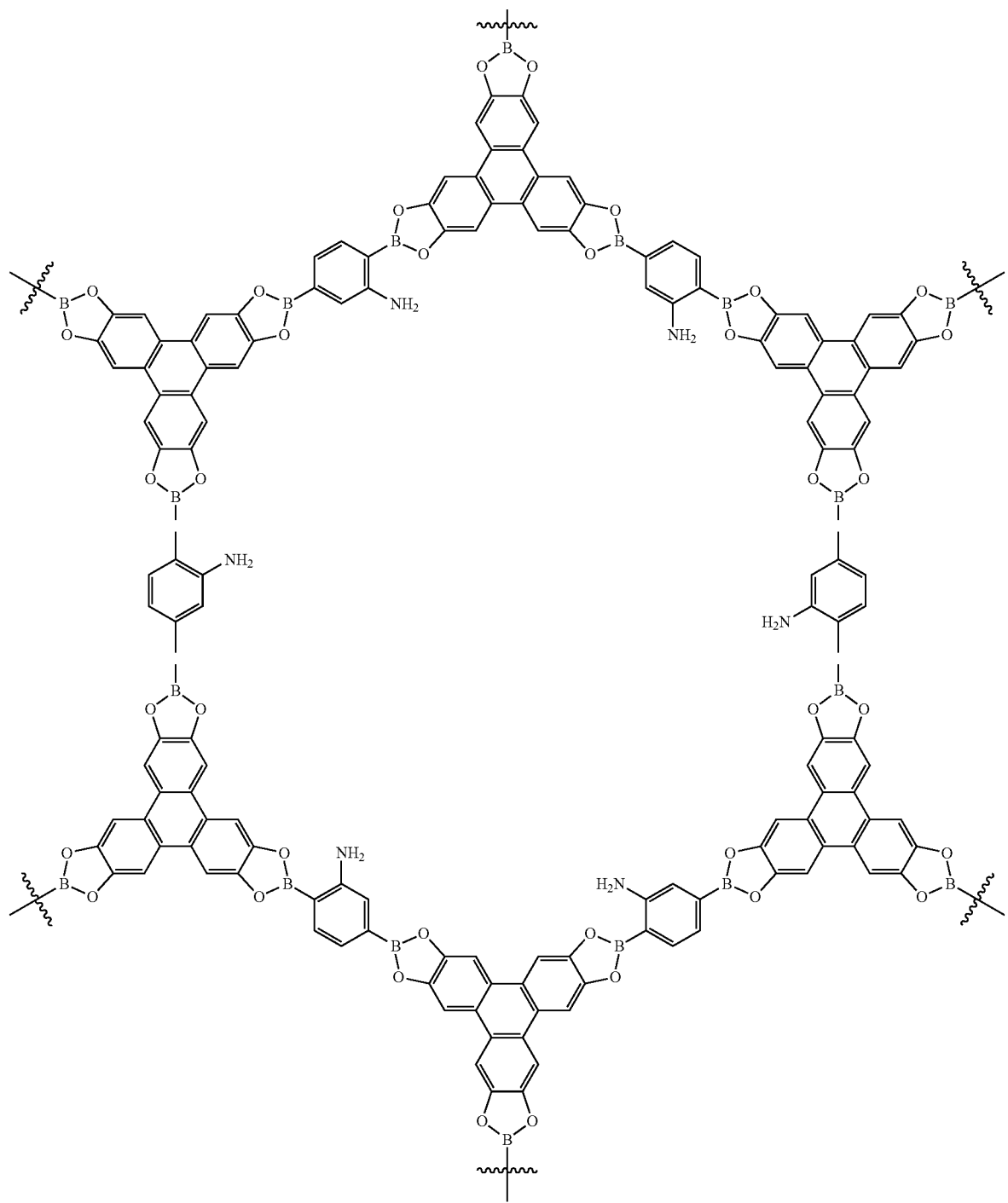
[Formula 18a]

Examples of the porous crystal in which borane is bonded to —NH$_2$ groups of Formulas 15a, 15b, and 16a through an additional chemical reaction include, but are not limited to, porous crystals represented by Formula 19 to Formula 24.
[Formula 19]
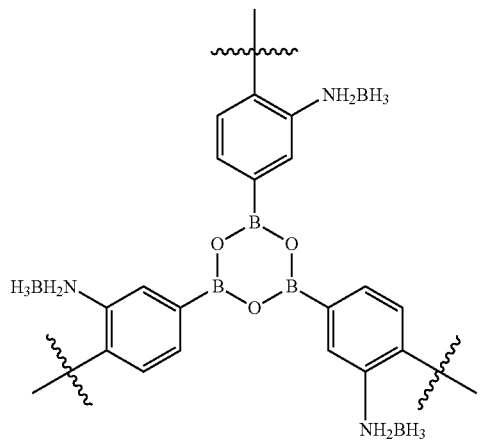
[Formula 20]
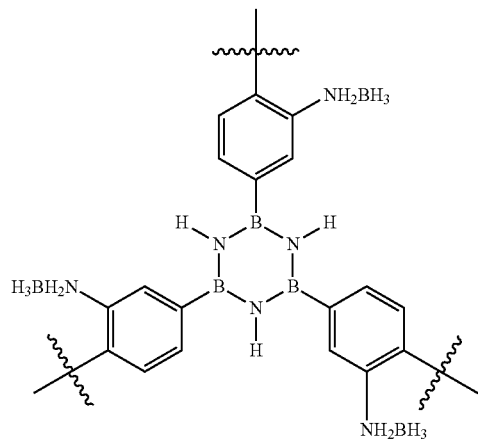
[Formula 21]
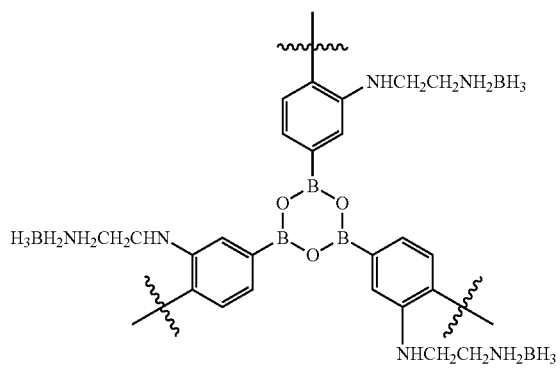
[Formula 22]
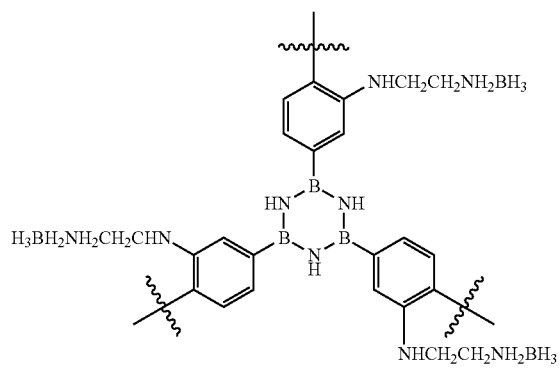
[Formula 23]
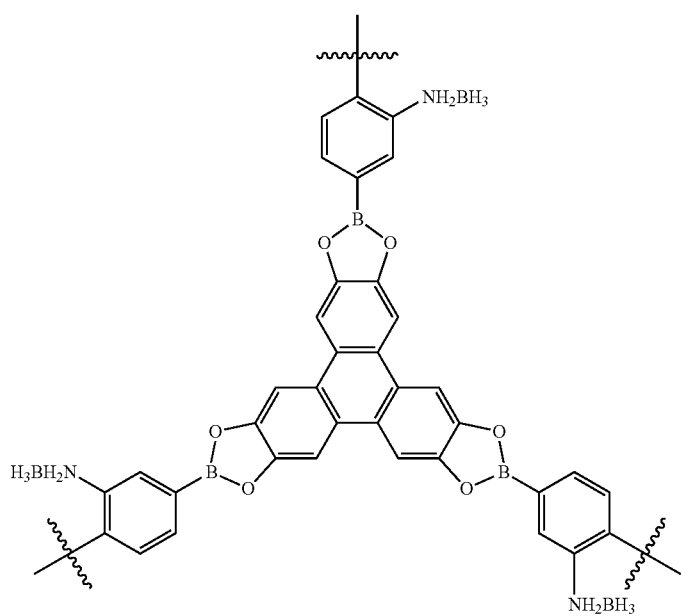

[Formula 24]

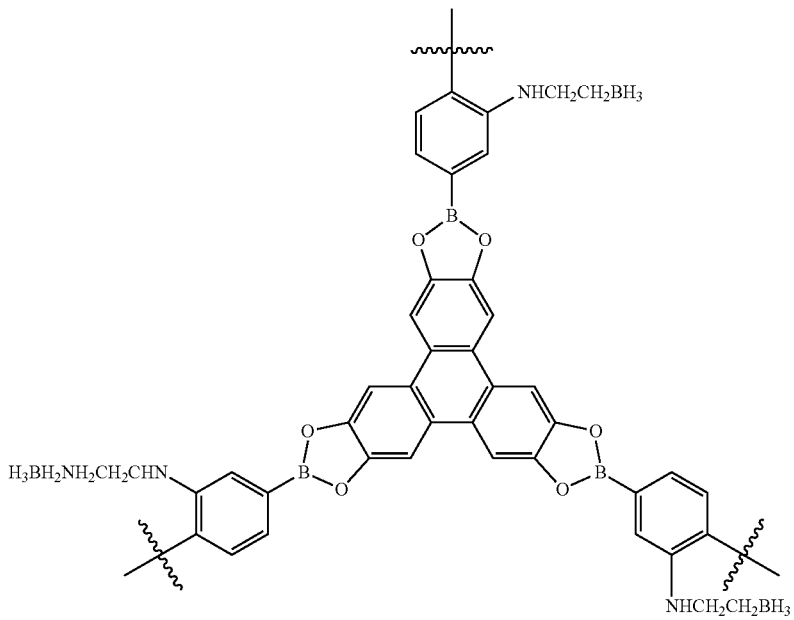

As an example of a method for preparing a porous crystal comprising ammonia borane according to the present invention, there is a method including preparing a porous crystal having a metal-organic framework or a covalent organic framework including primary amine; and adding borane or a derivative thereof to the porous crystal to bond the borane to an organic ligand of the porous crystal.

As another example of a method for preparing a porous crystal comprising ammonia borane according to the present invention, there is a method including preparing a porous crystal having a metal-organic framework or a covalent organic framework; adding an additional material, which can form a primary amine group by being chemically bonded to an organic ligand of the porous crystal, to the porous crystal to form a porous crystal including the primary amine group; and adding borane or a derivative thereof to the porous crystal including the primary amine group obtained in above step to chemically bond the borane to the primary amine group.

Hereinafter, the present invention will be described in detail with reference to Examples and Comparative Examples. However, the present invention is not limited thereto.

Example 1

10 ml of THF and 0.3 g of IRMOF-3 [$Zn_4O(C_8H_5NO_4)$] crystal were mixed with each other, and then, 1 equivalent of borane-THF complex (on the basis of the amine group of IRMOF-3) was added thereto at −78° C. This mixture was agitated for 24 hours at room temperature, and was filtered, and then, the formed crystal was separated. The separated crystal was cleaned by THF and dimethylchloride, was dried under vacuum, and was finally prepared into a porous crystal.

It was confirmed that the stretching vibration between B—H was shown at 2350 $cm^{-1}$ when ammonia borane was bonded to the metal-organic framework in the porous crystal prepared as described above by the IR spectrum.

Example 2

5 ml of toluene, 0.3 g of IRMOF-3 [$Zn_4O(C_8H_5NO_4)$] crystal, and 1 equivalent of 2-oxazolidine (on the basis of the amine group of IRMOF-3) were mixed with each other, and agitated at 110° C. for 24 hours.

This mixture was filtered to form a crystal, and then, the formed crystal was separated, was cleaned by dimethylchloride, and was dried under vacuum. After 8 ml of THF was mixed with 0.15 g of the obtained crystal, 1 equivalent of borane-THF complex (on the basis of the amine group of the obtained crystal) was added thereto at −78° C. This mixture was agitated for 24 hours at room temperature, and was filtered to form a crystal, and then, the formed crystal was separated. The separated crystal was cleaned by THF and dimethylchloride, was dried under vacuum, and was finally prepared into a porous crystal.

It was confirmed that the stretching vibration between B—H was shown at 2374 $cm^{-1}$ when ammonia borane was bonded to the metal-organic framework in the porous crystal prepared as described above by the IR spectrum.

Example 3

After 10 ml of THF and 0.24 g of the AmUMCM-1 [$(Zn_4O)_3(BDC-NH_2)_3(BTB)_4$] crystal were mixed with each other, 1 equivalent of borane-THF complex (on the basis of the amine group of AmUMCM-1) was added thereto at −78° C. This mixture was agitated for 24 hours at room temperature, and was filtered to form a crystal, and then, the formed crystal was separated. The separated crystal was cleaned by THF and dimethylchloride, was dried under the vacuum, and was finally prepared into a porous crystal.

It was confirmed that the stretching vibration between B—H was shown at 2333 $cm^{-1}$ when ammonia borane was bonded to the metal-organic framework in the porous crystal prepared as described above by the IR spectrum.

Example 4

5 ml of toluene, 0.48 g of AmUMCM-1 [$(Zn_4O)_3(BDC-NH_2)_3(BTB)_4$] crystal, and 1 equivalent of 2-oxazolidine (on the basis of the amine group of AmUMCM-1) were mixed with each other, and were agitated for 24 hours at 110° C.

This mixture was filtered to form a crystal, and then, the formed crystal was separated. The separated crystal was cleaned by dimethylchloride, and was dried under the vacuum. After 10 ml of THF was mixed with 0.23 g of the obtained crystal, 1 equivalent of borane-THF complex (on the basis of the amine group of the obtained crystal) was added thereto at −78° C. This mixture was agitated for 24 hours at room temperature, and was filtered to form a crystal, and then, the formed crystal was separated. The separated crystal was cleaned by THF and dimethylchloride, was dried under vacuum, and was finally prepared into a porous crystal.

It was confirmed that the stretching vibration between B—H was shown at 2353 cm$^{-1}$ when ammonia borane was bonded to the metal-organic framework in the porous crystal prepared described above by the IR spectrum.

The invention claimed is:

1. A porous crystal comprising ammonia borane, wherein the ammonia borane is chemically bonded thereto by a chemical reaction while a porous crystal structure is maintained.

2. The porous crystal comprising ammonia borane according to claim 1, wherein the porous crystal structure is a metal-organic framework or a covalent organic framework.

3. The porous crystal comprising ammonia borane according to claim 2, wherein the metal-organic framework comprises an organic ligand and a metal ion, and has a porous framework in which the organic ligand is chemically bonded to two or more metal ions, and the chemically bonded metal ion is serially chemically bonded to one or more other organic ligands.

4. The porous crystal comprising ammonia borane according to claim 2, wherein the covalent organic framework comprises an organic ligand, and has a porous framework in which the organic ligand is chemically bonded to two or more the same or different organic ligands, and the chemically bonded organic ligand is serially chemically bonded to two or more other organic ligands.

5. The porous crystal comprising ammonia borane according to claim 3, wherein the metal-organic framework is represented by the following Formula 1:

[Formula 1]

wherein M is one or more metals selected from the group consisting of metal belonging to Groups 3 to 16, lanthanium metal, and actinium metal, $L_1$ and $L_2$ are each independently

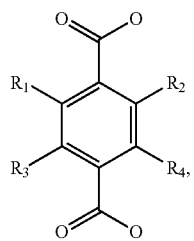

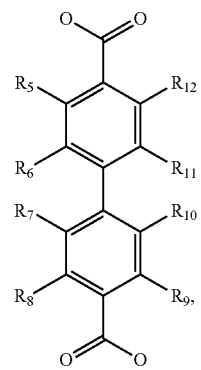

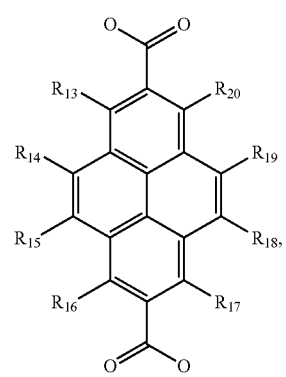

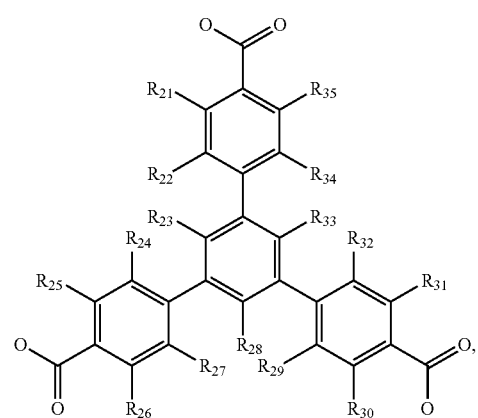

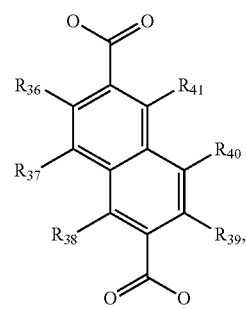

-continued

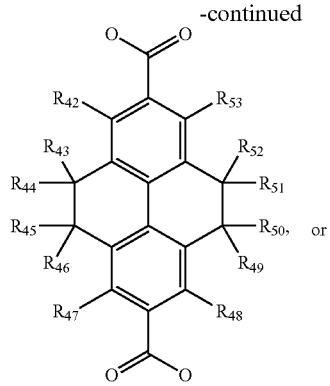

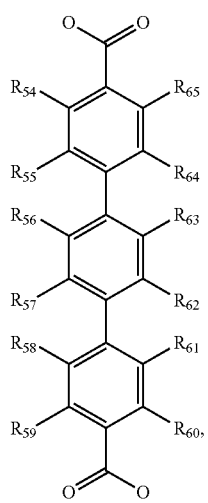

$R_1$ to $R_{65}$ are independently H; $NH_2$; $NHNH_2$; OH; COOH; CHO; CN; Cl; Br; I; NCO; OCN; $NCSNH_2$; alkyl that is substituted or unsubstituted by $NH_2$, $NHNH_2$, OH, COOH, CHO, CN, Cl, Br, I, $(C=O)_2O$, $(C=O)_2NH$, NCO, OCN or NCS; alkoxy; a functional group including sulfur; a functional group including Si; nitro; a functional group including boron; a functional group including phosphorus or an ester group, adjacent two of $R_1$ to $R_{65}$ groups may form a $(C=O)_2O$ (carboxylic acid anhydride) group or a $(C=O)_2NH$ (imide) group, in each L1 and L2, at least one of $R_1$ to $R_{65}$ is $NH_2$, OH, COOH, CHO, CN, Cl, Br, I, $(C=O)_2O$, $(C=O)_2NH$, NCO, OCN, NCS, or alkyl substituted with OH, COOH, CHO, CN, Cl, Br, I, NCO, OCN or NCS, z is an integer of 1 to ∞, a is 0<a≤100, b is 0≤b≤100, c is 0≤c≤300, d is 0≤d≤300, and at least one of c and d is not 0.

6. The porous crystal comprising ammonia borane according to claim 5, wherein the metal-organic framework is represented by the following Formula 2 or Formula 3:

[Formula 2]

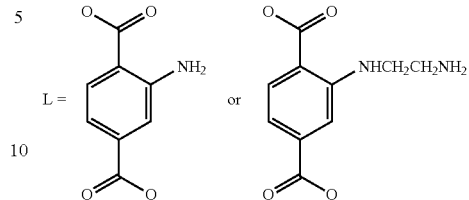

[Formula 3]

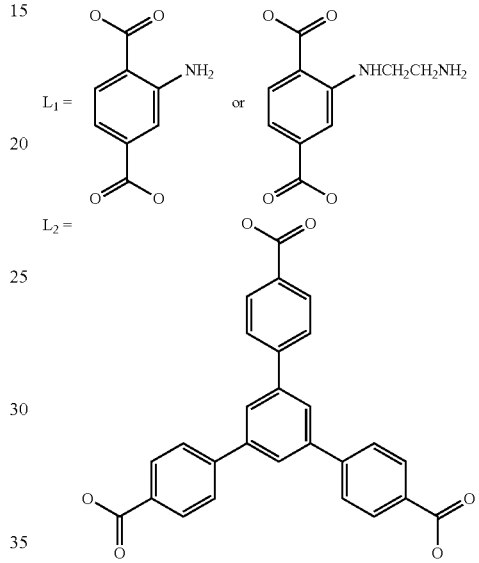

wherein n is an integer of 1 to ∞.

7. The porous crystal comprising ammonia borane according to claim 6, which is represented by any one of the following Formula 4 to Formula 7:

[Formula 4]

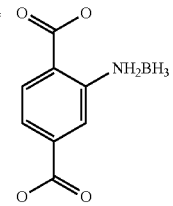

[Formula 5]

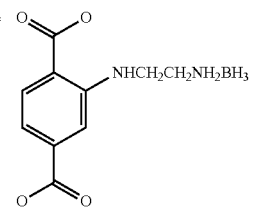

-continued

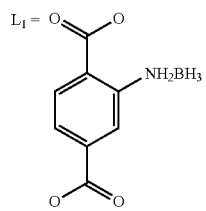

$[Zn_4O]_{3n}[(L_1)_3(L_2)_4]_n$, $L_1 =$

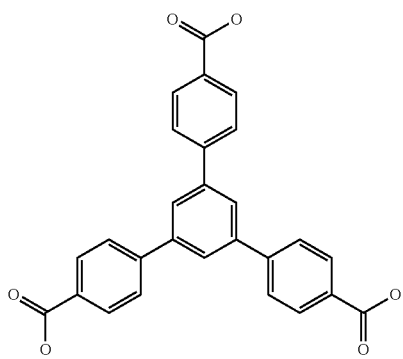

$L_2 =$

[Formula 6]

$[Zn_4O]_{3n}[(L_1)_3(L_2)_4]_n$, $L_1 =$

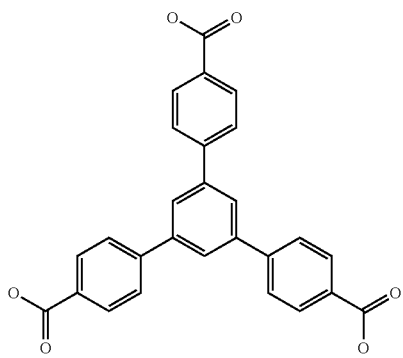

$L_2 =$

[Formula 7]

wherein n is an integer of 1 to ∞.

8. The porous crystal comprising ammonia borane according to claim 4, wherein the covalent organic framework a linear or cyclic boron-containing cluster represented by the following Formula 8 or Formula 9:

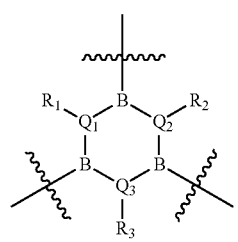

[Formula 8]

-continued

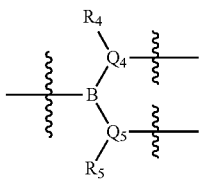

[Formula 9]

wherein $Q_1$ to $Q_5$ are each independently an element belonging to Group 15 or 16 of a periodic table, with proviso that when Q1 to Q2 are each independently an element of Group 15, $R_1$ to $R_5$ are each independently hydrogen, a $C_1$-$C_{12}$ alkyl group, a $C_6$-$C_{12}$ aryl group, or halogen, and when $Q_1$ to $Q_5$ are each independently an element of Group 16, $R_1$ to $R_5$ do not exist.

9. The porous crystal comprising ammonia borane according to claim 8, wherein the linear or cyclic boron-containing cluster is represented by the following Formulas:

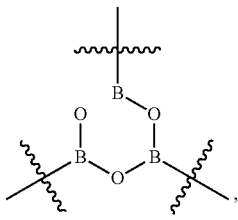

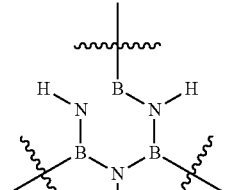

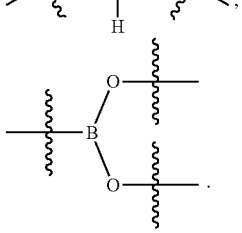

10. The porous crystal comprising ammonia borane according to claim 8, wherein the linear or cyclic boron-containing cluster is covalently bound to the same or different two or three aromatic cycle groups to form a building block.

11. The porous crystal comprising ammonia borane according to claim 10, wherein the aromatic cycle group is represented by any one of the following Formula 10 to Formula 14:

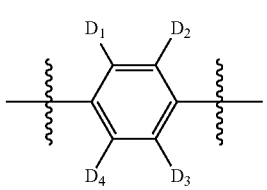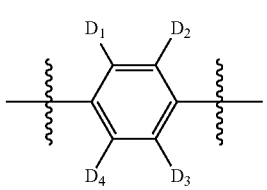

[Formula 10]

-continued

[Formula 11]

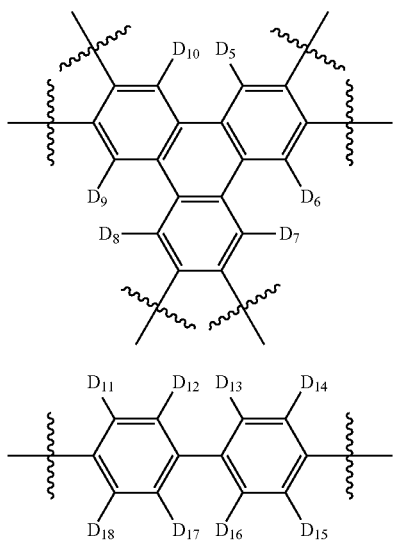

[Formula 12]

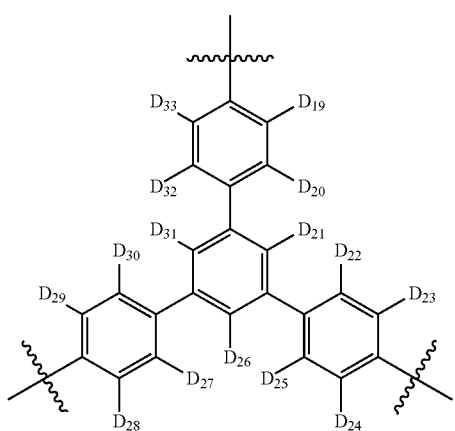

[Formula 13]

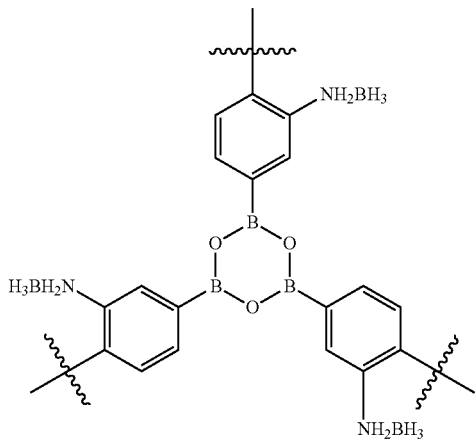

-continued

[Formula 14]

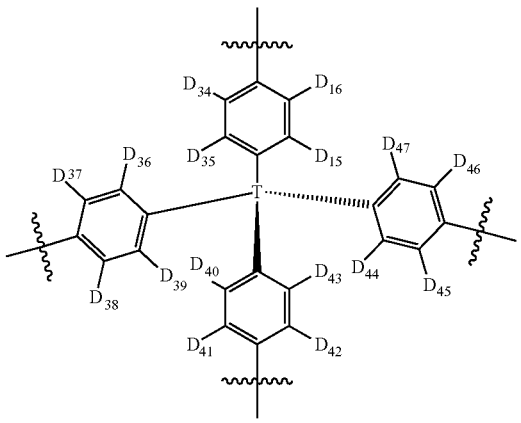

wherein

D$_1$ to D$_{47}$ are each independently a group selected from the group consisting of hydrogen; a C$_1$-C$_{12}$ alkyl group; a C$_1$-C$_{12}$ alkyl group substituted with one or more substituent groups selected from the group consisting of NH$_2$, NHNH$_2$, OH, COOH, CHO, CN, Cl, Br, I, (C=O)$_2$O, (C=O)$_2$NH, NCO, OCN, and NCS; a C$_6$-C$_{12}$ aryl group; a C$_1$-C$_{12}$ alkoxy group; NH$_2$; NHNH$_2$; OH; COOH; CHO; CN; Cl; Br; I; (C=O)$_2$O; (C=O)$_2$NH; NCO; OCN; NCS; a functional group including sulfur; a functional group including Si; nitro group; a functional group including boron; a functional group including phosphorus; and an ester group, T is an element that can form a regular tetrahedron structure, and in each aromatic cycle group, at least one of D$_1$ to D$_{47}$ should be NH$_2$; OH; COOH; CHO; CN; Cl; Br; I; (C=O)$_2$O; (C=O)$_2$NH; NCO; OCN; NCS; or a C$_1$-C$_{12}$ alkyl group substituted with one or more substituent groups selected from the group consisting of NH$_2$, OH, COOH, CHO, CN, Cl, Br, I, (C=O)$_2$O, (C=O)$_2$NH, NCO, OCN, and NCS.

12. The porous crystal comprising ammonia borane according to claim 11, which is represented by any one of the following Formula 19 to Formula 24:

[Formula 19]

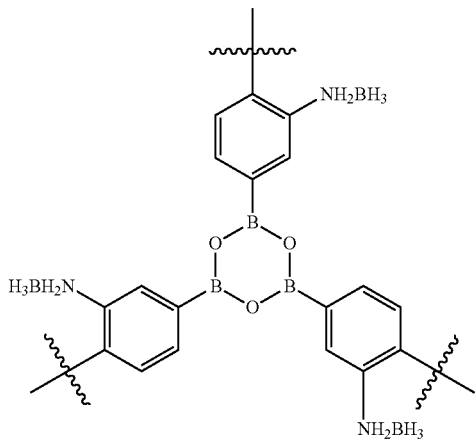

[Formula 20]

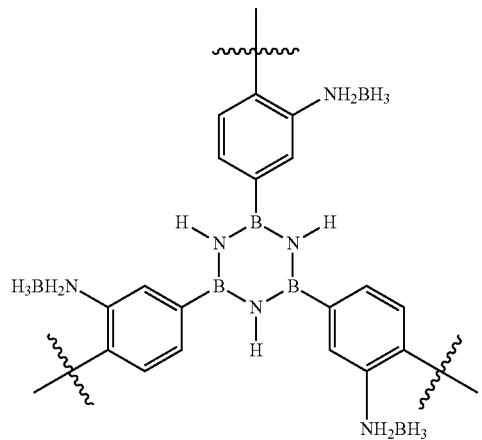

[Formula 21]
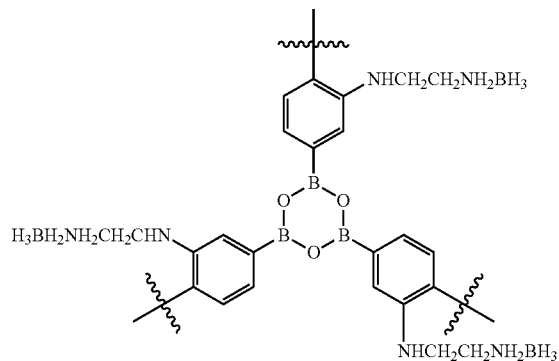
[Formula 22]
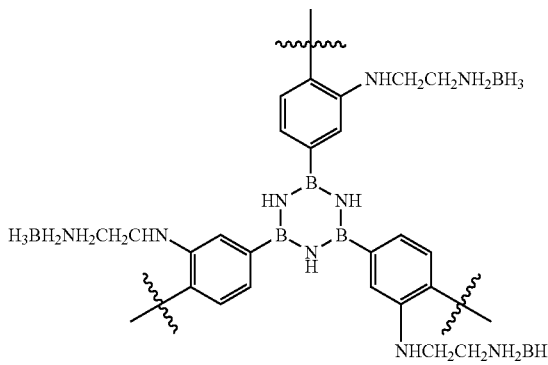
[Formula 23]
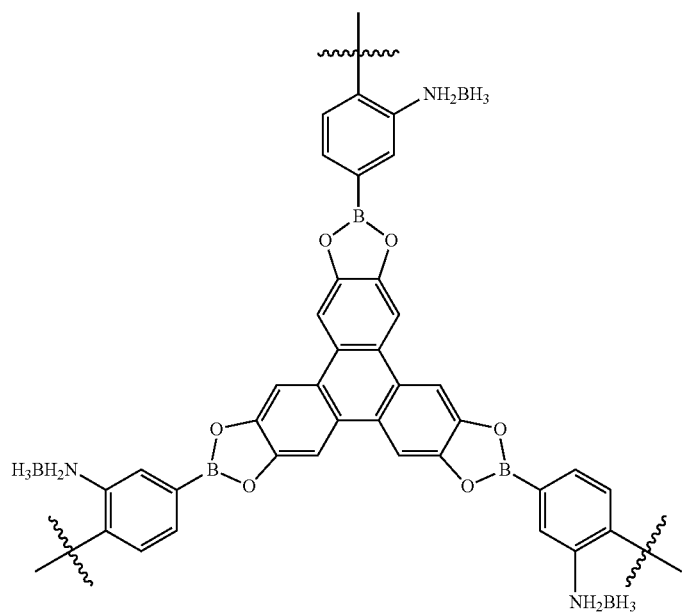
[Formula 24]
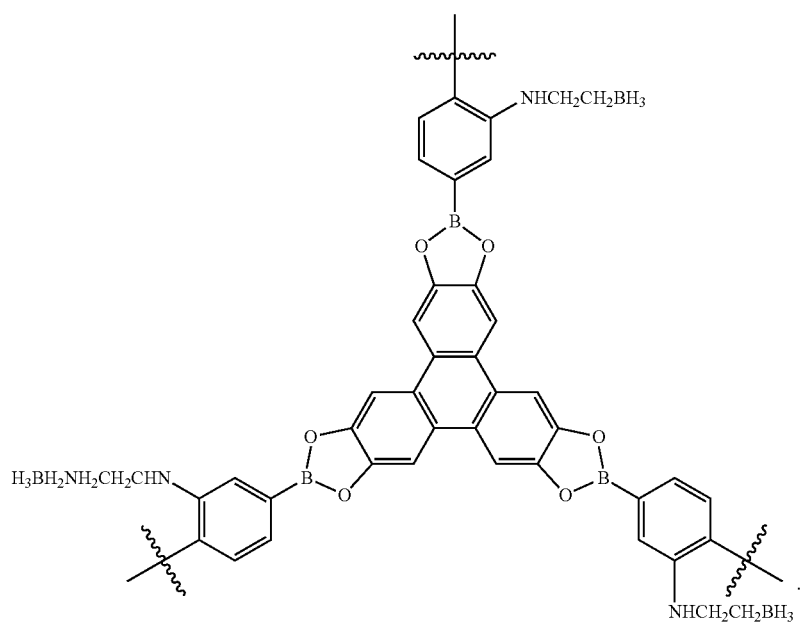

13. The porous crystal comprising ammonia borane according to claim 1, which is used as a storage material of hydrogen.

14. A method for producing a porous crystal comprising ammonia borane, comprising:
   preparing a porous crystal having a metal-organic framework or a covalent organic framework comprising primary amine; and
   adding borane or a borane derivative to the porous crystal to bind the borane to an organic ligand of the porous crystal.

15. A method for producing a porous crystal comprising ammonia borane, comprising:
   preparing a porous crystal having a metal-organic framework or a covalent organic framework;
   adding an additional material, which can form primary amine group by being chemically bonded to the organic ligand of the porous crystal to the porous crystal, to form a porous crystal including the primary amine group; and
   adding borane or a derivative thereof to the porous crystal including the primary amine group obtained in the above-step to chemically bond the borane to the primary amine group.

\* \* \* \* \*